US012685455B2

(12) United States Patent
Lane

(10) Patent No.: US 12,685,455 B2
(45) Date of Patent: Jul. 21, 2026

(54) METHODS AND APPARATUS FOR TRANSDERMAL MEASUREMENT OF IMPEDANCE

(71) Applicant: Zelemiq Life Science Limited, Salisbury (GB)

(72) Inventor: Rodney Paul Lane, Salisbury (GB)

(73) Assignee: Zelemiq Life Science Limited, Salisbury (GB)

( * ) Notice: Subject to any disclaimer, the term of this patent is extended or adjusted under 35 U.S.C. 154(b) by 267 days.

(21) Appl. No.: 18/270,973

(22) PCT Filed: Jan. 27, 2022

(86) PCT No.: PCT/EP2022/051870
§ 371 (c)(1),
(2) Date: Jul. 5, 2023

(87) PCT Pub. No.: WO2022/175051
PCT Pub. Date: Aug. 25, 2022

(65) Prior Publication Data
US 2024/0049975 A1 Feb. 15, 2024

(30) Foreign Application Priority Data

Feb. 22, 2021 (GB) ..................................... 2102479

(51) Int. Cl.
*A61B 5/0531* (2021.01)
*A61B 5/00* (2006.01)
(52) U.S. Cl.
CPC .......... *A61B 5/0531* (2013.01); *A61B 5/6833* (2013.01)
(58) Field of Classification Search
CPC ... A61B 5/0531; A61B 5/6833; A61B 5/0533; A61B 5/14546; A61B 5/28; A61B 5/291;
(Continued)

(56) References Cited

U.S. PATENT DOCUMENTS 5,795,293 A 8/1998 Carim et al.
6,517,482 B1 2/2003 Elden et al.
(Continued)

FOREIGN PATENT DOCUMENTS

CA 2633827 A1 6/2007
JP 2002501802 A 1/2002
JP 2019523428 A 8/2019

OTHER PUBLICATIONS

Chizmadzhev, Yuri A., Andrey V. Indenbom, Peter I. Kuzmin, Sergey V. Galichenko, James C. Weaver, and Russell O. Potts. "Electrical properties of skin at moderate voltages: contribution of appendageal macropores." Biophysical Journal 74, No. 2 (1998): 843-856.

(Continued)

*Primary Examiner* — Eric F Winakur
*Assistant Examiner* — Sienna C Pyle
(74) *Attorney, Agent, or Firm* — Smartpat PLC

(57) ABSTRACT

The present invention relates to a non-invasive transdermal apparatus for measuring complex impedance of body tissue. The apparatus comprises: at least two electrodes coupled, in use, to the surface of the skin; a signal source to deliver an electrical potential to the electrodes; a monitor to detect changes in the signal passing through body tissue between the electrodes; and a processor operatively coupled to the signal source and monitor and configured to: use the signal source to apply a potential to the electrodes to reduce the electrical impedance of the stratum corneum; and use the monitor to measure complex transdermal impedance AC signals corresponding to $\alpha$ and $\beta$ dispersion spectra.

18 Claims, 5 Drawing Sheets

(58) Field of Classification Search
        CPC ....... A61B 5/296; A61B 5/297; A61B 5/4845;
                        A61B 5/681; A61B 5/14532; A61B
                                        5/0537; A61B 5/25
        See application file for complete search history.

(56)                              References Cited

U.S. PATENT DOCUMENTS

| | | | |
|---|---|---|---|
| 8,903,484 B2 | 12/2014 | Mazar | |
| 2009/0281404 A1 | 11/2009 | Currie et al. | |
| 2012/0101351 A1* | 4/2012 | Caduff ................. | A61B 5/0531 |
| | | | 600/347 |
| 2025/0025078 A1* | 1/2025 | Kendall ............. | A61B 5/14514 |

OTHER PUBLICATIONS

Podtaev, Sergey, D. Nikolaev, V. Samartsev, Vasily Gavrilov, and Kirill Tsiberkin. "Frequency and temperature dependence of skin bioimpedance during a contralateral cold test." Physiological measurement 36, No. 3 (2015): 561.
Japanese Patent Office, Notice of Reasons for Refusal in related Japanese Patent Application No. 2023-574753, English Machine Translation obtained from USPTO Global Dossier, Nov. 12, 2025.

* cited by examiner

METHODS AND APPARATUS FOR TRANSDERMAL MEASUREMENT OF IMPEDANCE

CROSS-REFERENCE TO RELATED APPLICATION

This application is a national stage application, filed under 35 U.S.C. § 371, of International Patent Application PCT/EP2022/051870, filed on Jan. 27, 2022, which claims the benefit of United Kingdom Patent Application GB 2102479.9, filed on Feb. 22, 2021.

TECHNICAL FIELD

The present invention relates to methods and apparatus for non-invasive transdermal measurement of complex impedance of body tissue.

BACKGROUND

The measurement of impedance of body tissue has been found to be useful in a variety of medical monitoring applications.

For example, U.S. Pat. No. 5,795,293 discloses systems and methods for monitoring bioelectric signals. Such biosignals are generally bioelectrical signals which are time-varying and are produced by specialised body tissue, organs, or cell systems. Common biosignals include, for example: Electroencephalogram (EEG); Electrocardiogram (ECG); Electromyogram (EMG); Electrooculogram (EOG); Electroretinogram (ERG); Electrogastrogram (EGG); and Galvanic skin response (GSR) or electrodermal activity (EDA). Biosignals are typically measured transdermally via electrodes attached to the skin of a subject.

Impedance may also be used for active measurement of body tissue by introducing a measuring signal transdermally into the tissue and detecting the resultant response. Such techniques may potentially be used for determining the levels of substances in the body tissue, for example the concentration of a substance in the blood. For example, U.S. Pat. No. 8,903,484 discloses a method and apparatus for measuring impedance as a measure of a patient's hydration and respiration.

Despite the useful applications there is currently an absence of readily commercially available methods or apparatus that provide reliable measurement of complex impedance of body tissue in a non-invasive transdermal manner. Clearly reliable and effective techniques would be beneficial. For example, there is a general demand for wearable devices (such as smart-watches) which can provide health monitoring functionality. Further there are several health conditions that require regular monitoring and may benefit from the continuous monitoring which can only be provided by a wearable (or implantable devices which have significant drawbacks over external transdermal devices). For example, Diabetes is one of the leading causes of death and illness worldwide and its prevalence is growing significantly. Managing blood glucose levels is essential in the control of diabetes. Such management usually requires direct blood testing which may for example be carried out using a finger pricker to extract a blood droplet or by using an implantable device or patch.

It will therefore be appreciated that there is a desire to provide non-invasive transdermal ways to monitor blood substances such as glucose levels. U.S. Pat. No. 6,517,482 proposes a method and apparatus for determining glucose levels based upon measurements of skin tissue impedance. This has not, however, resulted in any commercially available devices or methods. Further, this patent does not appear to necessarily provide a practical solution which could be implemented in a wearable device or the like as the skin surface on which electrodes are to be placed must be treated with a saline solution and electrically conductive gel.

SUMMARY

According to a first aspect of the invention, there is provided a non-invasive transdermal apparatus for measuring complex impedance of body tissue, the apparatus comprising: at least two electrodes coupled, in use, to the surface of the skin (of a subject); a signal source to deliver an electrical potential to the electrodes; a monitor to detect changes in the signal passing through body tissue between the electrodes; and a processor operatively coupled to the signal source and monitor and configured to: use the signal source to apply a potential to the electrodes to reduce the electrical impedance of the stratum corneum; and use the monitor to measure complex transdermal impedance AC signals corresponding to $\alpha$ and $\beta$ dispersion spectra.

According to another aspect of the invention there is provided a method of non-invasive transdermal measurement of complex impedance of body tissue, the method comprising the steps of: coupling at least two electrodes to the skin of the subject; applying a potential to the electrodes to reduce the electrical impedance of the stratum corneum; and monitoring complex transdermal impedance AC signals corresponding to $\alpha$ and $\beta$ dispersion spectra.

Without being bound to any specific theory, the applicant has recognised that a limitation on prior methods and apparatus appear to result from the effective layer provided by the upper portions of the skin, particularly the stratum corneum. The impedance of the stratum corneum layer (at approximately at $10^5$ $\Omega cm^2$ and 30 $nF/cm^2$) is several orders of magnitude higher than that of the underlying tissue. The insulative layer effect causes attenuation in biosignals when measuring transdermally and has limited the types of measurements possible by current methods. When exposed to an alternating current (AC) signal the insulative effect of the stratum corneum layer acts in a similar manner to a capacitor and the impairment of such signals will be most significant for lower frequency signals. As a result, there is currently no reliable way of transdermally measuring complex impedance in body tissue at frequencies below around 10 kHz (which corresponds to lower ends of $\beta$ dispersion spectra and all regions of the $\alpha$ dispersion spectra).

Embodiments of the invention advantageously address these problems by apply a potential to the skin through the electrodes to reduce the effective electrical impedance of the stratum corneum. This then enables more effective monitoring of both biosignals from the body and impedance measurements through the skin including the monitoring of signals corresponding to $\alpha$ and $\beta$ dispersion spectra.

In some embodiments the AC signals may have a frequency of less than 10 kHz. For example, the AC signals have a frequency of between approximately 1 kHz and 1 GHz (and may for example be between 10 kHz and 100 Hz).

The apparatus may also monitor AC signals corresponding to $\gamma$ dispersion spectra. Such $\gamma$ dispersion spectra occur above 100 MHz and may therefore be measurable by existing methods but embodiments of the invention may advantageously measure all of the defined dispersion regions (i.e. $\alpha$, $\beta$ and $\gamma$).

The applicant has identified that the electrical potential required to achieve the reduction in electrical impedance of the stratum corneum may be considered to be a function of the required potential per bi-layer multiplied by the number of bi-layers (the skilled person may appreciate that the stratum corneum comprises between 70 to 100 lipid and corneocyte bi-layers). As such, in embodiments the potential applied to the electrodes may be between 1 V and 150 V. More specifically the electrical potential may be between 14 V and 40 V.

In embodiments the electrodes may have a uniform electrical impedance of a magnitude close to that of the stratum corneum of human skin. For example, the impedance of the electrodes is approximately $10^5$ $\Omega cm^2$. The applicant has found that when the potential is applied the preferential conduction pathways of the hair follicles and sweat glands are prevented from becoming the only connection between the inner and out layers of the lipid-corneocyte.

The processor may use the electrodes to input a common signal to provide a potential to reduce electrical impedance of the stratum corneum and to provide a measurement input signal. Alternatively, the processor may use the electrodes to input separate signals to provide a potential to reduce electrical impedance of the stratum corneum and to provide a measurement input signal.

The processor may use the monitor to detect and/or measure phase angle shift in the electrical signal. Phase angle shift has been found by the applicants to provide a highly promising indicator for example as use in detecting blood glucose levels. It is believed that the use of phase angle shift as a measures is directly enabled by the increased sensitivity in signals provided in embodiments of the invention as a result of the reduction in electrical impedance of the stratum corneum.

In some embodiments the processor may use the reduction in impedance of the body tissue to enhance detection of biosignals from the subject. The biosignals may include one or more of: Electroencephalogram (EEG), Electrocardiogram (ECG), Electromyogram (EMG), Electrooculogram (EOG), Electroretinogram (ERG), Electrogastrogram (EGG), Galvanic skin response (GSR) or electrodermal activity (EDA).

The processor may use the complex impedance of body tissue to measure impedance variations indicative of at least one target substance in the body. The at least one target substances may include one or more of blood sugar, blood alcohol or cholesterol.

The apparatus may comprise a wearable device. A wearable device may be a permanent or semi-permanent patch or the like or a device in a form such as a watch or pedant. A wearable device may for example have electrodes arranged on a skin facing surface such that they are held in contact with the subject skin in use.

The apparatus may further comprise a memory, coupled to the processor, for storing measurements. The apparatus may further comprise an indicator or display. The apparatus may include a wireless communication transmitter, for example a wireless transmitter (which may use Wi-Fi, Bluetooth or other communication protocols). The apparatus may further comprise a power source, for example a rechargeable battery.

Methods in accordance with embodiments may comprise the step of applying a potential to the electrodes further comprises simultaneously applying a measurement input signal. The step of monitoring complex transdermal impedance AC signals corresponding to $\alpha$ and $\beta$ dispersion spectra may further comprises monitoring AC signals corresponding to $\alpha$ dispersion spectra.

The step of monitoring may comprise detecting and/or measure phase shift in the electrical signal.

Methods in accordance with embodiments may further comprises using the complex impedance of body tissue to detect biosignals from the subject. Methods of embodiments may further comprises using the complex impedance of body tissue to measure impedance variations indicative of at least one target substance in the body.

Whilst the invention has been described above, it extends to any inventive combination of the features set out above or in the following description or drawings.

Unless otherwise stated, each of the integers described may be used in combination with any other integer as would be understood by the person skilled in the art. Further, although all aspects of the invention preferably "comprise" the features described in relation to that aspect, it is specifically envisaged that they may "consist" or "consist essentially" of those features outlined in the claims. In addition, all terms, unless specifically defined herein, are intended to be given their commonly understood meaning in the art.

Further, in the discussion of the invention, unless stated to the contrary, the disclosure of alternative values for the upper or lower limit of the permitted range of a parameter, is to be construed as an implied statement that each intermediate value of said parameter, lying between the smaller and greater of the alternatives, is itself also disclosed as a possible value for the parameter.

In addition, unless otherwise stated, all numerical values appearing in this application are to be understood as being modified by the term "about".

BRIEF DESCRIPTION OF THE DRAWINGS

Embodiments of the invention may be performed in various ways, and embodiments thereof will now be described by way of example only, reference being made to the accompanying drawings, in which.

DETAILED DESCRIPTION

Embodiments are described below but for context and to provide a clear understanding of the operation of the invention skin structure and properties will be explained with reference to FIGS. 1 to 4.

The body produces measurable electric signal known a bio-signals that can be passively detected with use of the appropriate equipment. Techniques also exist for making active measurements of body tissue by introducing electrical signals into the body to measure the response. In either case it is preferable that the methods are carried out transdermally (i.e. through the skin from the exterior surface) to provide methods and apparatus for non-invasive testing/monitoring. However, as explained further below transdermal measurement methods are affected by the electrical impedance of the skin, which can significantly impair the both the scope and effectiveness of such methods. One approach to reduce such affects is to abrade the skin prior to taking measurements but this then becomes an invasive procedure which can cause discomfort and skin irritation. Accordingly, embodiments of the invention seek to provide methods and apparatus which remain truly non-invasive.

Figure 1:
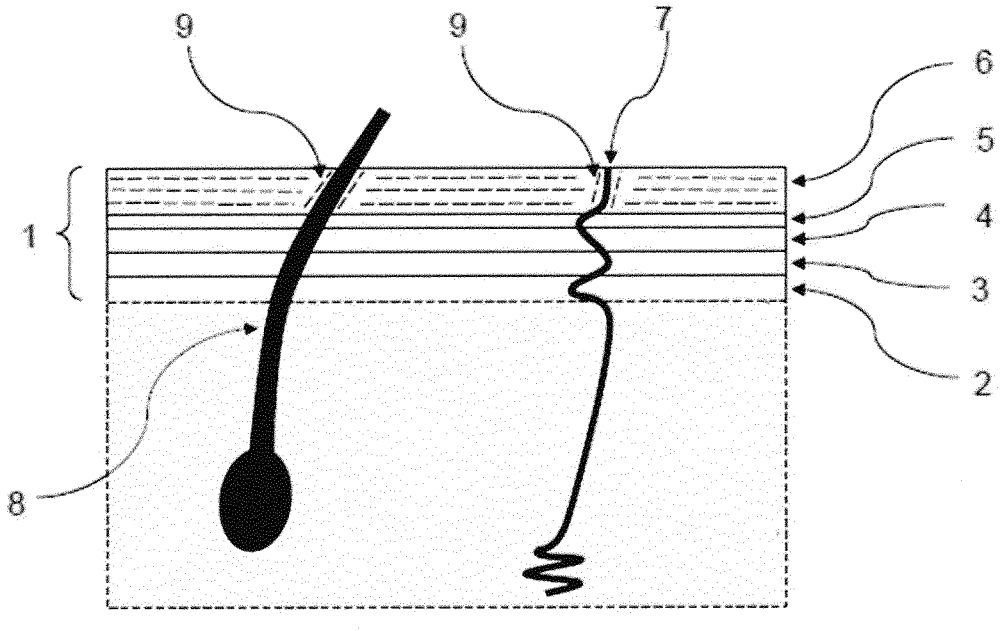
FIG. 1 shows a cross sectional diagram representing the structure of human skin tissue.

As shown in FIG. 1, the skin or the epidermis 1 is made up from up to five layers. The stratum basale 2 is the deepest layer of epidermis and consists of cuboidal and columnar cells. The stratum spinosum 3 consisting of skin cells that are connected by desmosomes adhesive protein complexes local to intercellular junctions, responsible for maintaining the mechanical integrity of tissue. The stratum granulosum 4 consists of skin cells with components that contribute to the formation of the outer skin layer. The stratum lucidum 5 is a specialist shear layer only present on the palms and soles of feet. The stratum corneum 6: this is the outermost layer of skin consisting of very tough specialised skin cells that have the function of protecting the other layers of the epidermis.

Figure 2:
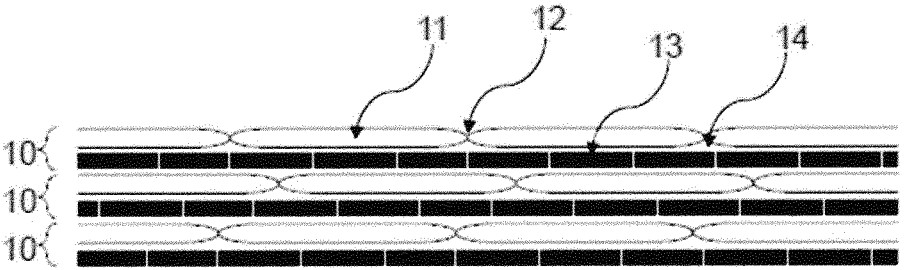
FIG. 2 illustrates the structure of the stratum corneum.

Of all the layers the stratum corneum 6 represents the greatest impedance barrier for electrical signal to pass through the skin. As shown in FIG. 2, the stratum corneum is formed from Keratinocytes which are created in the lower layers of the epidermis and then pushed up to the stratum corneum 6 where they transform into corneocytes 11 which have a very durable cell envelope. Corneocytes 11 can be compared to 'bricks' because of the way that the are tightly packed together in anywhere from 15 to 40 layers to form the dense outer protective covering to the skin. The gaps between successive layers of coenocytes is filled with lipids 13 that have been released from tiny lamellar bodies within the stratum granulosum 4. The lipids can loosely be compared to 'mortar' between the 'bricks' of the lipid-corneocyte matrix.

The combination of a tightly packed layers of corneocytes 11 and lipids 13 forms a high impedance layer which prevents the easy flow of electrical signal.

The impedance of the stratum corneum 6 layer (at approximately $10^5$ $\Omega cm^2$ and 30 nF/cm²) is several orders of magnitude higher than that of the underlying tissue from where bio-signals are produced. To prevent unacceptable levels of attenuation when collecting biosignals it is generally necessary for existing measuring equipment to have a very much higher input impedance than the stratum corneum. Although effective this method significantly limits the type of measurement that can be made.

In addition to detecting biosignals body impedance is a potentially useful measure in health applications. As the stratum corneum 6 provides an effective insulation layer to heavily impede the flow of direct current (DC) signals making measurements of body impedance using DC voltage is ineffective. However as this outer layer of the epidermis 1 behaves in a manner similar to a capacitor when exposed to an alternating current (AC) signals it has been found that AC voltage can be used to measure the 'complex impedance' of the body. A complex impedance measurement made in this way will contain information about the purely resistive components and those due to the capacitive elements know as reactance.

Unfortunately as the frequency of the AC signal used for the measurement is reduced and tends towards becoming DC the effectiveness of the method is impaired before becoming entirely ineffective. An understanding of the behaviour of the tissue is required to fully explain the implications of this effect.

Typical biological tissue has three defined regions of dispersion that are known as the α, the β and γ dispersion regions. The lowest frequency a-dispersion occurs with AC measuring signals that are below 1 kHz. It is driven by interface polarisation effects from the flow of ions across cell membranes.

The α dispersion is associated with frequency-dependent conductance of the protein channels within the cell membranes, frequency-dependent counter-ion environment near the charged cell surface, and endoplasmic-reticulum effect in contractile tissue.

The β dispersion or mid-frequency dispersion occurs at AC measurement frequencies of around 300 kHz. It arises due to the electrical polarisation of the cellular plasma membranes that act as barriers to the flow of ions between the intra and extra cellular space. Cell diameter, membrane capacitance, and fluid conductivity determines the effect. Along with any contribution from polarisation of proteins and organic macromolecules.

The γ dispersion or high frequency dispersion occurs above 100 MHz. It is contributed to largely by relaxation of polar water molecules.

The skin impedance problems discussed above mean that complex impedance measurement using AC signals using prior art methods will begin to be impaired from 10 kHz at the lower end of the β dispersion region, and that exist prior art methods are largely ineffective by the time the α dispersion region is reached below 1 kHz. As such, prior art methods currently provide no reliable way of making transdermal complex impedance measurements of body tissue within the lower end of the β dispersion region or within any of the α dispersion region.

The applicant has now identified that the application of a potential to the skin can temporarily reduce the electrical impedance of the stratum corneum and enable improved measuring/monitoring of transdermal impedance. Without being bound by any specific theory, the underlying cause of this reduction in electrical impedance will now be explained to assist in understanding of the invention.

Human skin is around 1 mm in thickness with the stratum corneum 6 making up the outermost 10 to 40 μm. As shown in FIG. 2, the corneocytes 11 are approximately hexagonal in shape 30 μm across and 1 μm deep, they are organised into the stratum corneum 6 in closely stacked flat layers. The corneocytes are bound together at junctions known as corneodesmosomes 12. The remaining extracellular space is filled with highly electrically conductive salt ions 14. Between each layers of corneocytes cells there is a layer specialised lipids 13 that contain sphingolipids, fatty acids, and cholesterols. The stratum corneum comprises of between 70 to 100 or these lipid and corneocyte bi-layers 10, a structure referred to as the lipid-corneocyte matrix.

Figures 3A, 3B:
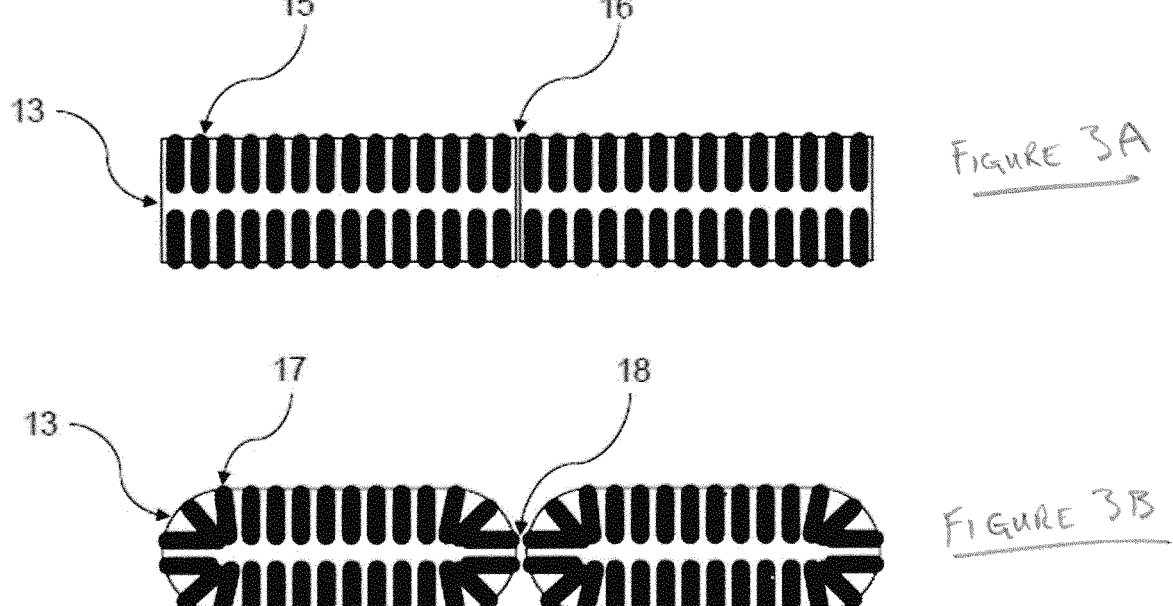
FIGS. 3A and 3B respectively represent the lipid layer when pores on the outer surface are hydrophobic and hydrophilic.

As illustrated in FIG. 3A, in response to lateral thermal fluctuation of the lipid molecules 13 within the bi-layers 10, hydrophobic pores are formed on the outer membrane of the lipids 15. These pores being hydrophobic seek to become arranged with the inner part of the pore repelled from each other. This causes the lipids to take on a rectangular profile that becomes tightly arranged 16, and closing off any gap between the adjacent layers of corneocyte cells within the bi-layer stack of the lipid-corneocyte matrix.

As represented in FIG. 3B, when a voltage with a potential difference of between 200 to 400 mV is applied across a bi-layer of corneocytes cells and lipids 10, the previously hydrophobic pores on the lipid membranes become hydrophilic 17 and therefore attracted to each other. This causes the ends of the lipid profile to become rounded 18, which in turn permits the extracellular salt ions to make connection between the bi-layers of the lipid-corneocyte matrix, and greatly reducing the impedance to the flow of electric signals across the bi-layer.

The applicant has recognised that when this process is repeated across all of the bi-layers of the lipid-corneocyte matrix 6 the electrical impedance of the stratum corneum can become reduced by several orders of magnitude. The electrical potential required to achieve this is function of the required potential per bi-layer multiplied by the number of bi-layers. A potential of between 1 V and 150 V may be sufficient to provide such an effect and in particular a potential of between 14 and 40 V may effectively achieve this effect.

Figure 4:
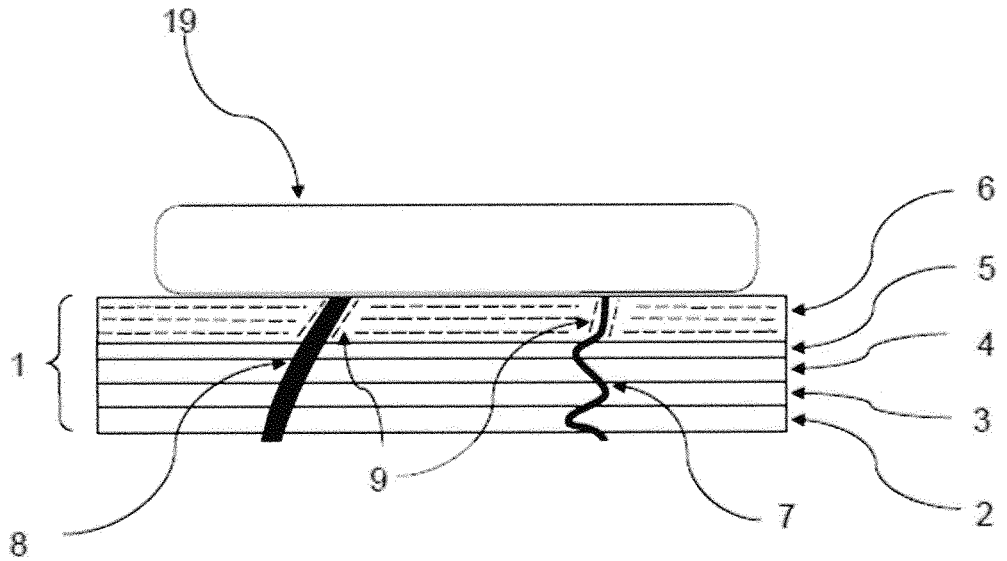
FIG. 4 illustrates a transdermal electrical connection on the surface of a region of skin tissue.

As seen in FIGS. 1 and 4, an additional feature of skin that needs to be considered are the areas where the stratum corneum is crossed by hair follicles 8 and the shafts of sweat glands 7. In these regions the corneocytes are aligned normal to these follicle or shaft 9 meaning that the number of cells making up the thickness across of the stratum corneum is greatly reduced in these areas. The consequence is that these regions of the stratum corneum represent preferential current paths for electricity through the skin, with significant reductions in impedance achieved by applying potentials much lower than required for the flat layers of the lipid-corneocyte matrix.

A uniform lowering of impedance in the stratum corneum lipid-corneocyte matrix is a key contributory factor in achieving the improved measurement of bio-signals and complex impedance measurements of the body. The applicant has, therefore, recognised that it is advantageous to ensure that when the electrical potential required to cause a reduction in impedance is applied across the stratum corneum, that the preferential conduction pathways of the hair follicles and sweat glands are prevented from becoming the only connection between the inner and out layers of the lipid-corneocyte.

In embodiments of the invention, this can be achieved by use of electrical connections 19 to the skin surface that have an inbuilt uniform electrical impedance of a magnitude that is similar to the stratum corneum 6. This results in more even charge distribution, because if current attempts to preferentially flow along the path of the hair follicles and sweat glands 9 the internal impedance of the material used in the electrical connection to the skin 19 will result in a lowering of the potential difference at these regions, preventing any significant increased flow of current. This allows the electrical charge to build to a level high enough to achieve the required potential across the lipid-corneocyte matrix of the stratum corneum 6 to enable the hydrophobic pores 15 within the lipid 13 to become hydrophilic 17. Allowing the openings 18 of the barrier between the corneocyte layers 11 which become filled by the salt ions 14 to provide an electrical conduction pathway through the stratum corneum 6.

Figure 5:
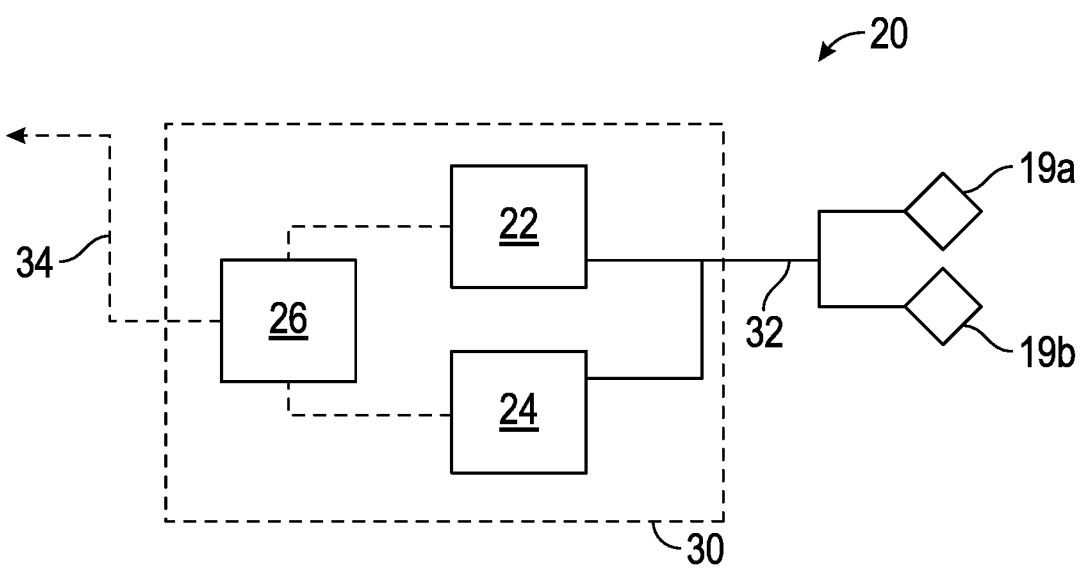
FIG. 5 schematically represents an apparatus in accordance with a first embodiment.

In order to take advantage of the effects described above, embodiments of the invention may provide a non-invasive transdermal apparatus 20 for measuring complex impedance of body tissue as shown in FIG. 5. The apparatus includes or is connected to at least two electrodes 19a, 19b which are coupled in use to the surface of the subject's skin. It may be appreciated that the type of apparatus will determine whether the electrodes 19 are permanently attached to the apparatus or are removable/replaceable (for example single use hygienic electrode patches) that are attached to the apparatus by a lead or wire 32.

The apparatus further comprises a signal source 22 coupled to the electrodes 19a, 19b (for example via lead 32) and configured to delivering an electric potential to the electrodes. A monitor 24 is also couple to the electrodes 19a, 19b to detect changes in signals passing though body tissue between the electrodes 19a, 19b. It will be appreciated that the changes in signals detected by the monitor may include both changes in impedance resulting from a signal input by the device and/or biosignals naturally occurring in the body.

A processor 26 is provided which controls the source 22 and monitor 24. The processor 26 is configured to use the signal source 22 to apply a potential to the electrodes to reduce the electrical impedance of the stratum corneum. The processor 26 is also configured to use the monitor 24 to measure complex transdermal impedance AC signals corresponding to $\alpha$ and $\beta$ dispersion spectra. The processor 26, signal source 22 and monitor 24 may be integrated into a control system 30 of the apparatus 20.

The apparatus 20 may further includes an output 34 for providing data on measured signals. It will be appreciated that depending upon the type of apparatus 20 the output could be raw data on impedance measurements or may be correlated data on a measure such as data on biosignals in the subject body or on target substances in the substance body. In some embodiments both raw and interpreted data may be output. The output 34 could be directed to a display or other human interface. Alternatively or additionally, the output can include an output interface such as a wireless communication transmitter to pass measured data to a computer, mobile phone or other device.

Figure 6:
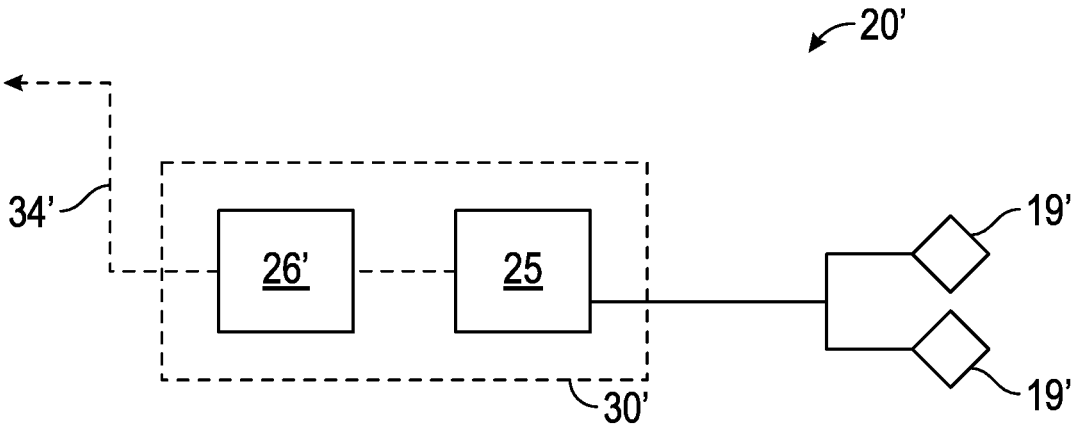
FIG. 6 schematically represents an apparatus in accordance with a second embodiment.

FIG. 6 shows an alternate apparatus 20' in which the signal source 22 and monitor 24 of FIG. 5 are integrated into a single component 25 which both provides the impedance lowering potential and measures impedance signals from the electrodes 19'.

Figure 7:
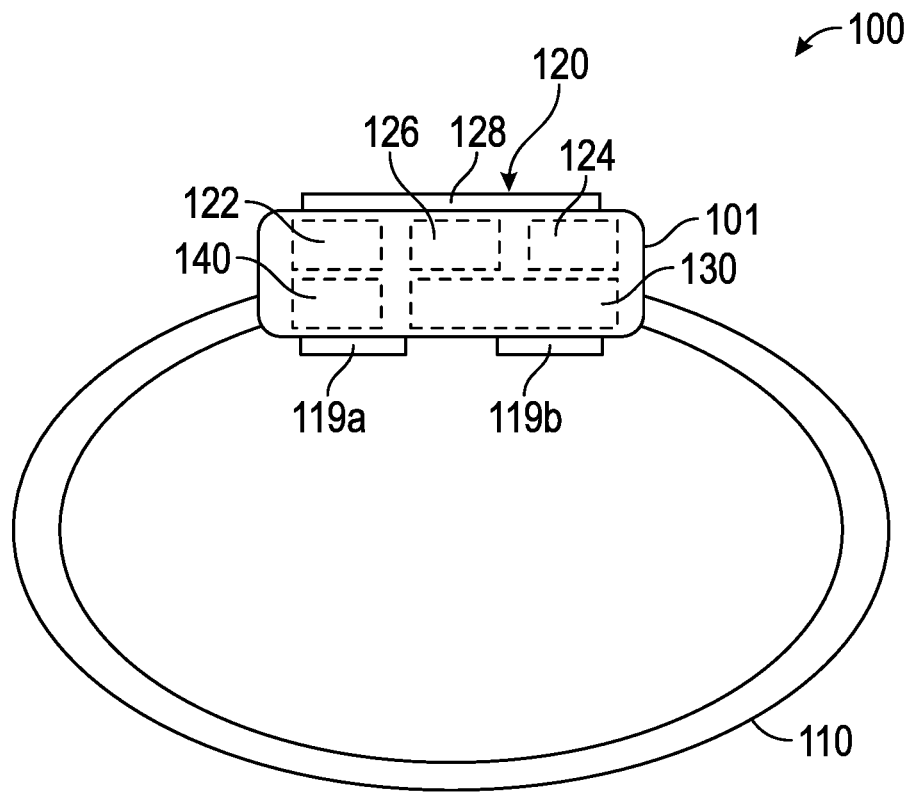
FIG. 7 represents a wearable device in accordance with an embodiment of the invention.

FIG. 7 provides an example of a wearable device 100 incorporating an apparatus 120 in accordance with embodiments of the invention. In this example the wearable 100 is arranged as on a band 110 which can be worn for example around a person's wrist (as such the wearable may be considered to be a watch or smartwatch). The band 110 is attached to a housing 101 having a display 128 (for example an LCD or OLED) on the exterior surface and a pair of spaced apart electrodes 119a and 119b on the interior, skin facing surface. Within the housing there is provided a power sources 130 such as a battery, a processor 126, a signal source 122, a monitor 124 and a communications chip 140 (for example an NFC, wireless or Bluetooth interface). It will be appreciated the electronic components of the wearable device 100 may be integrated into a single processor or chip. The wearable device 100 may also include machine readable storage for holding data resulting from the signal monitoring.

Although the invention has been described above with reference to preferred embodiments, it will be appreciated that various changes or modification may be made without departing from the scope of the invention as defined in the appended claims. For example, whilst the wearable device described above is in the form of a wrist worn device, other devices could be arranged for example a wearable pendant or patch.

The invention claimed is:

1. A non-invasive transdermal apparatus for measuring complex impedance of body tissue, the apparatus comprising:

at least two electrodes coupled, in use, to the surface of the skin of a subject;

a signal source to deliver an electrical potential to the electrodes;

a monitor to detect changes in a signal passing through body tissue between the electrodes; and a processor operatively coupled to the signal source and to the monitor and configured to:

use the signal source to apply a potential to the electrodes to reduce an electrical impedance of the stratum corneum; and use the monitor to measure complex transdermal impedance AC signals corresponding to both:

α dispersion spectra below 1 kHz, and

β dispersion spectra below 10 KHz.

2. The apparatus of claim 1, wherein the apparatus also monitors AC signals corresponding to γ dispersion spectra.

3. The apparatus of claim 1, wherein the potential applied to the electrodes to reduce the electrical impedance of the stratum corneum is between 1 V and 150 V.

4. The apparatus of claim 1, wherein the electrodes have a uniform electrical impedance of a magnitude close to that of the stratum corneum of human skin.

5. The apparatus of claim 1, wherein the processor is configured to use the electrodes to input a common signal to provide a potential to reduce electrical impedance of the stratum corneum and to provide a measurement input signal.

6. The apparatus of claim 1, wherein the processor is configured to use the electrodes to input separate signals to provide a potential to reduce electrical impedance of the stratum corneum and to provide a measurement input signal.

7. The apparatus of claim 1, wherein the processor is configured to use the monitor to detect and/or measure phase shift in the electrical signal.

8. The apparatus of claim 1, wherein the processor is configured to use the complex transdermal impedance AC signals to detect biosignals from the subject.

9. The apparatus of claim 8, wherein the biosignals include one or more of: Electroencephalogram (EEG), Electrocardiogram (ECG), Electromyogram (EMG), Electrooculogram (EOG), Electroretinogram (ERG), Electrogastrogram (EGG), Galvanic skin response (GSR) or electrodermal activity (EDA).

10. The apparatus of claim 1, wherein the processor is configured to use the complex impedance of body tissue to measure impedance variations indicative of at least one target substance in the body.

11. The apparatus of claim 10, wherein the at least one target substance includes one or more of blood sugar, blood alcohol, and cholesterol.

12. The apparatus of claim 1, wherein the apparatus comprises a wearable device.

13. A method of non-invasive transdermal measurement of complex impedance of body tissue, the method comprising the steps of:

coupling at least two electrodes to the skin of a subject;

applying a potential to the electrodes to reduce an electrical impedance of the stratum corneum; and monitoring complex transdermal impedance AC signals corresponding to α dispersion spectra below 1 kHz, and β dispersion spectra below 10 KHz.

14. The method of claim 13, wherein the step of applying a potential to the electrodes further comprises simultaneously applying a measurement input signal.

15. The method of claim 13, wherein the step of monitoring complex transdermal impedance AC signals corresponding to α and β dispersion spectra further comprises monitoring AC signals corresponding to γ dispersion spectra.

16. The method of claim 13, wherein the step of monitoring comprises detecting and/or measuring phase shift in the electrical signal.

17. The method of claim 13, wherein the method further comprises using the complex impedance of body tissue to detect biosignals from the subject.

18. The method of claim 13, wherein the method further comprises using the complex impedance of body tissue to measure impedance variations indicative of at least one target substance in the body.

* * * * *